United States Patent
Komura et al.

(10) Patent No.: US 7,845,208 B2
(45) Date of Patent: Dec. 7, 2010

(54) APPARATUS AND METHOD FOR DETECTING VOLATILE DISSOLVED SUBSTANCE

(75) Inventors: Hajime Komura, Mishima-gun (JP); Kazuo Onaga, Osaka (JP); Hiroshi Koda, Sanda (JP)

(73) Assignee: Suntory Holdings Limited, Osaka (JP)

( * ) Notice: Subject to any disclaimer, the term of this patent is extended or adjusted under 35 U.S.C. 154(b) by 859 days.

(21) Appl. No.: 11/631,070

(22) PCT Filed: Jun. 30, 2005

(86) PCT No.: PCT/JP2005/012055

§ 371 (c)(1),
(2), (4) Date: Dec. 28, 2006

(87) PCT Pub. No.: WO2006/003982

PCT Pub. Date: Jan. 12, 2006

(65) Prior Publication Data

US 2009/0188299 A1    Jul. 30, 2009

(30) Foreign Application Priority Data

Jul. 2, 2004    (JP)    ............... 2004-197086

(51) Int. Cl.
*G01N 1/00*    (2006.01)
*G01N 33/00*    (2006.01)
(52) U.S. Cl. ..................................... 73/19.01; 422/68.1
(58) Field of Classification Search ............... 73/19.01, 73/19.02, 23.41, 61.55; 422/68.1
See application file for complete search history.

(56) References Cited

U.S. PATENT DOCUMENTS 2,987,912 A * 6/1961 Jacobson ..................... 73/19.1

(Continued)

FOREIGN PATENT DOCUMENTS

JP    2530416/07-055659    3/1995

(Continued)

OTHER PUBLICATIONS

Urabe et al., "Josuijo Gensui no Biryo Yubun Kanshi System", Yokogawa Giho, vol. 42, No. 4, Oct. 1998, p. 1.

*Primary Examiner*—Lisa M Caputo
*Assistant Examiner*—Punam Roy
(74) *Attorney, Agent, or Firm*—The Webb Law Firm

(57) ABSTRACT

An apparatus for detecting a volatile dissolved substance includes a sample vessel 1 capable of holding therein an approximately fixed amount of liquid A, B with leaving a space at an upper inner section thereof; a nozzle 4 capable of blowing off bubbles into the liquid held in the sample vessel, and a pressurized gas feeding device L capable of feeding pressurized gas to the nozzle for the blowing of the bubbles. Within a communication passage 5 communicating with the upper section of the sample vessel, there is exposed a detecting portion of a sensor S capable of detecting a volatile component, so that the sensor can detect the volatile component which has evaporated from the liquid in the sample vessel and entered the communication passage. The apparatus further includes a liquid vessel 2, 3 capable of holding the liquid therein, a feeding mechanism D capable of feeding the liquid of the liquid vessel to the sample vessel and an overflow mechanism E for causing an amount of the liquid exceeding the approximately fixed amount to overflow from the sample vessel to the outside of the vessel.

7 Claims, 12 Drawing Sheets

U.S. PATENT DOCUMENTS

| | | | |
|---|---|---|---|
| 3,740,320 A * | 6/1973 | Arthur | 435/39 |
| 4,740,356 A * | 4/1988 | Huber | 422/81 |
| 5,127,259 A * | 7/1992 | Kahl et al. | 73/19.1 |
| 5,222,032 A * | 6/1993 | Fleming | 700/271 |
| 5,604,297 A * | 2/1997 | Seiden et al. | 73/19.1 |
| 5,807,699 A * | 9/1998 | Nason et al. | 435/32 |
| 6,235,207 B1 * | 5/2001 | Conrad | 210/742 |
| 6,312,606 B1 * | 11/2001 | Conrad | 210/742 |

FOREIGN PATENT DOCUMENTS

| | | |
|---|---|---|
| JP | 07-054841 | 12/1995 |
| JP | 08-105881 | 4/1996 |
| JP | 11-083701 | 3/1999 |
| JP | 3554761/11-326170 | 11/1999 |
| JP | 2001-272321 | 10/2001 |
| WO | WO 2005068989 A1 * | 7/2005 |

* cited by examiner

FIG.1

APPARATUS AND METHOD FOR DETECTING VOLATILE DISSOLVED SUBSTANCE

TECHNICAL FIELD

The present invention relates to an apparatus and a method for detecting a volatile dissolved substance. The apparatus includes or the method employs a sample vessel capable of holding therein an approximately fixed amount of liquid with leaving a space at an upper inner section thereof a nozzle capable of blowing off bubbles into the liquid held in the sample vessel, and a pressurized gas feeding device capable of feeding pressurized gas to said nozzle for the blowing of the bubbles. Within a communication passage communicating with the upper section of the sample vessel, there is exposed a detecting portion of a sensor capable of detecting a volatile component. In operation, the sensor can detect the volatile component which has evaporated from the liquid in the sample vessel and entered the communication passage.

BACKGROUND ART

For example, mineral water is made into a commercial product through various processes such as special filtration, sedimentation, heat sterilization, etc. effected on raw mater obtained from a specified water source or spring. In this regard, if a transporting vessel and/or storage vessel for the raw water or a pipeline used in bottling is/are contaminated with microorganism, chemical substance or the like or if other commercial article, a cleaning agent, or the like remains in e.g. the bottling pipeline, this can sometimes add stench or unwanted flavor to the product to be obtained.

Further, since soft drink products such as juice are also made mainly from water, such causes as above can sometimes add stench thereto.

With some types of contaminants, even such a trace amount thereof as one-millionth or less, is felt as stench. Therefore, prevention, monitoring and control against mixing of stench giving substance or flavoring agent are very important. Further, if waste water generated from a sewage plant or various industrial plants contains any stenchful or odorous substance remaining therein, this gives significant trouble and health hazard to local inhabitants. Hence, management of stenchful substance in waster water is also important.

For the above reasons, human sensory evaluation testing has been conducted as means for detecting stench or unwanted flavor. However, with food processing plants, sewage plants and various industrial plants, the atmosphere therein is often filled with odorous components. Thus, the sensory evaluation test, if conducted on site at such places, often suffers low accuracy due to the masking effect from the atmosphere therein. In addition, it may be said that the sensory evaluation test lacks objectivity, since there occurs irregularity in the evaluation result depending on the physical condition of the evaluating panelists.

On the other hand, as an evaluation testing method using machinery, a gas chromatography device, a gas chromatography/mass spectrometer, or the like are often employed. Most of these machines are highly sensitive machines capable of detecting as little as 0.1 ng of sample of each component for most kinds of compounds. However, these machines are sophisticated and expensive machines requiring special knowledge for their operations. Therefore, these machines cannot not be installed in a process in a plant or processing plate for easy operation. Moreover, as these machines require a significant amount of time and labor from preprocessing of a sample to be determined to result evaluation, they are not suitable for use for occasions or sections where the result is needed immediately.

On the other hand, as a sensor for detecting a volatile component in natural atmosphere, there are known a metal oxide semiconductor type gas sensor, a hot-wire gas sensor, a solid electrolyte type gas sensor, an infrared type gas sensor, etc. These gas sensors are compact, inexpensive and can be easily handled as well. However, as these sensors are affected by temperature variation, humidity variation of the atmosphere, unwanted gas mixed in the atmosphere, etc., such sensors alone cannot be used for detection of a trace amount of volatile organic compound contained in such atmospheres as above. Then, for instance, the metal oxide semiconductor type gas sensor capable of detecting gaseous species with the highest precision can detect a volatile component at a ppb (one-billionth) level under an atmospheric condition with exclusion of the variable factors such as temperature, humidity, mixing gas, etc.

The convention has proposed also a detecting apparatus for a volatile dissolved substance so that a volatile dissolved substance contained in liquid such as raw water can be positively evaporated for detection by means of a relatively simple sensor which is compact, low-priced and can be handled relatively easily, even when the sensor is used in a process conducted in a plant or processing plant whose atmosphere is filled with a significant amount of odorous or unwanted flavoring component. This detecting apparatus includes a sample vessel capable of holding therein an approximately fixed amount of liquid with leaving a free space at an upper inner section thereof, a nozzle capable of blowing off bubbles into the liquid held in the sample vessel, and a pressurized gas feeding device capable of feeding pressurized gas to said nozzle for the blowing of the bubbles. Within a communication passage communicating with the upper section of the sample vessel, there is exposed a detecting portion of a sensor capable of detecting a volatile component. In operation, the sensor can detect the volatile component which has evaporated from the liquid in the sample vessel and entered the communication passage. Namely, according to this conventional detecting apparatus, for enabling precision detection of the volatile component under a predetermined condition, a pre-measured, approximately fixed amount of liquid is charged into the sample vessel, so that the volatile component evaporated from this approximately fixed amount of liquid may be detected by the sensor (see e.g. Patent Document 1).

Patent Document Japanese Patent Application "Kokai" No. 11-83701

DISCLOSURE OF THE INVENTION

Object to be Achieved by Invention

At a liquid-handling site such as a industrial factory or processing plant, there is a need for easy detection of the volatile component, when needed, without requiring any special skill or experience. However, with the above-described conventional detecting apparatus, as a pre-measured, approximately fixed amount of liquid is charged into the sample vessel for the detection, depending on the detecting personnel, the amount of liquid charged in the sample vessel can be too large or too small, thus there is the risk of failure in the precision detection of the volatile component under the predetermined condition.

The present invention has been made in view of the above-described state of the art. The object of the invention is to allow easy and precision detection of a volatile component under a predetermined condition, when needed, without requiring any special skill or experience.

Means for Achieving the Object

According to a first characterizing feature of the present invention, an apparatus for detecting a volatile dissolved substance, comprises:

a sample vessel capable of holding therein an approximately fixed amount of liquid with leaving a space at an upper inner section thereof;

a nozzle capable of blowing off bubbles into the liquid held in the sample vessel;

a pressurized gas feeding device capable of feeding pressurized gas to said nozzle for the blowing of the bubbles.

within a communication passage communicating with the upper section of the sample vessel, there being exposed a detecting portion of a sensor capable of detecting a volatile component, so that the sensor can detect the volatile component which has evaporated from the liquid in the sample vessel and entered the communication passage;

a liquid vessel capable of holding the liquid therein;

a feeding mechanism capable of feeding the liquid of said liquid vessel to said sample vessel; and an overflow mechanism for causing an amount of the liquid exceeding said approximately fixed amount to overflow from said sample vessel to the outside thereof.

[Function and Effect]

As there are provided a liquid vessel capable of holding the liquid therein, a feeding mechanism capable of feeding the liquid of the liquid vessel to the sample vessel and an overflow mechanism for causing an amount of the liquid exceeding the approximately fixed amount to overflow from the sample vessel to the outside thereof, when the liquid of the liquid vessel is fed to the sample vessel by the feeding mechanism, if this liquid, in its amount, exceeds the approximately fixed amount and its excess amount is caused to overflow from the sample vessel, so that the sample vessel may hold the approximately fixed amount of liquid remaining therein.

Therefore, without effecting a measurement in advance, an approximately fixed amount of liquid can be charged into the sample vessel, so that precision detection is readily possible, when needed, under the predetermined condition, without requiring any special skill or experience.

According to a second characterizing feature of the present invention, said overflow mechanism includes an overflow pipe communicated and connected with said sample vessel, said overflow pipe incorporating an openable/closable valve.

[Function and Effect]

Since the overflow mechanism includes an overflow pipe communicated and connected with said sample vessel, the excess amount of liquid over the appropriately fixed amount can overflow through the overflow pipe from the sample vessel to the outside of the vessel.

Further, as the overflow pipe incorporates an openable/closable valve, after the approximately fixed amount of liquid has entered the sample vessel, the overflow pipe can be closed so as to prevent the atmosphere outside the vessel from entering the sample vessel through the overflow pipe. As a result, the volatile component can be detected with even higher precision.

According to a third characterizing feature of the present invention, the apparatus further comprises a valve mechanism capable of selectively connecting a liquid feeding passage from the liquid vessel to the sample vessel or a liquid discharging passage communicated to the outside of the vessel to a lower end portion of the sample vessel.

[Function and Effect]

As there is provided a valve mechanism capable of selectively connecting a liquid feeding passage from the liquid vessel to the sample vessel or a liquid discharging passage communicated to the outside of the vessel to a lower end portion of the sample vessel, when the liquid is to be fed from the liquid vessel to the sample vessel, the liquid feeding passage can be communicated and connected to the lower end of the sample vessel for feeding the liquid thereto. Also, when the liquid of the sample vessel is to be discharged to the outside of the vessel, the liquid discharging passage can be communicated and connected to the lower end of the sample vessel for discharging the liquid therefrom. In this way, the feeding and discharging operations of the liquid to/from the sample vessel can be carried out conveniently and easily.

Alternatively, there may be provided a valve mechanism capable of selectively connecting either a liquid feeding passage from the liquid vessel for pure water such as distilled water, ion exchanged water, to the sample vessel or a liquid discharging passage communicated to the outside of the vessel, to a lower end portion of the sample vessel. In this case, after feeding the pure water to the sample vessel, by discharging this water, the sample vessel can be cleaned conveniently and easily.

According to a fourth characterizing feature of the present invention, said feeding mechanism is constructed such that this feeding mechanism is capable of feeding the liquid to said sample vessel as said pressurized gas feeding device feeds the pressurized gas to the liquid vessel.

[Function and Effect]

For constructing the feeding mechanism, the pressurized gas feeding device capable of feeding the blowing pressurized gas to the nozzle capable of blowing off the bubbles in the liquid in the sample vessel is effectively utilized so that this pressurized gas feeding device can feed the pressurized gas to the liquid vessel, whereby the liquid of the liquid vessel can be fed to the sample vessel. Therefore, the construction of the feeding mechanism can be simplified.

According to a fifth characterizing feature of the present invention, the apparatus compares detection result obtained by said sensor for a reference volatile component evaporated from a reference liquid with detection result obtained by said sensor for a target volatile component evaporated from a detection target liquid, thus detecting the volatile dissolved substance in the liquid.

[Function and Effect]

As the volatile dissolved substance in the detection target liquid can be detected through comparison between detection result obtained by the sensor for a reference volatile component evaporated from a reference liquid with detection result obtained by said sensor for a target volatile component evaporated from a detection target liquid, it is possible to detect easily and quantitatively that the detection target liquid contains, as dissolved therein, a volatile dissolved substance other than the volatile dissolved substance dissolved in the reference liquid or that the detection target contains, as dissolved therein, a same volatile dissolved substance as that dissolved in the reference liquid, but the former being greater in amount than the latter.

According to a sixth characterizing feature of the present invention, said sample vessel is capable of selectively holding therein an approximately fixed amount of the reference liquid or an approximately fixed amount of the detection target liquid.

[Function and Effect]

As the sample vessel is configured to be capable of selectively holding therein an approximately fixed amount of the reference liquid or an approximately fixed amount of the detection target liquid, this sample vessel can hold both the reference liquid and the detection target liquid for a same approximately fixed mount. Also, the construction can be simplified.

According to a seventh characterizing feature of the present invention, there are provided, separately from each other, a reference liquid vessel capable of holding the reference liquid therein and a detection target liquid vessel capable of holding the detection target liquid therein, and said feeding mechanism is capable of selectively feeding the reference liquid of the reference liquid vessel or the detection target liquid of the detection target vessel.

[Function and Effect]

The reference liquid vessel capable of holding the reference liquid therein and the detection target liquid vessel capable of holding the detection target liquid therein are provided separately of each other and the feeding mechanism is configured to be capable of selectively feeding the reference liquid of the reference liquid vessel or the detection target liquid of the detection target vessel. Therefore, if the reference liquid is held in the reference liquid vessel and the detection target liquid is held in the detection target vessel, both the reference liquid and the detection target liquid can be fed and held for a same approximately fixed amount in the sample vessel, without requiring any operation by the detection personnel.

According to an eighth characterizing feature of the present invention, a method for detecting a volatile dissolved substance, the method using:

a sample vessel capable of holding therein an approximately fixed amount of liquid with leaving a space at an upper inner section thereof;

a nozzle capable of blowing off bubbles into the liquid held in the sample vessel;

a pressurized gas feeding device capable of feeding pressurized gas to said nozzle for the blowing of the bubbles.

within a communication passage communicating with the upper section of the sample vessel, there being exposed a detecting portion of a sensor capable of detecting a volatile component, so that the sensor can detect the volatile component which has evaporated from the liquid in the sample vessel and entered the communication passage;

wherein the method further uses a liquid vessel capable of holding the liquid therein and a feeding mechanism capable of feeding the liquid of said liquid vessel to said sample vessel, so that an amount of the liquid exceeding said approximately fixed amount is caused to overflow from said sample vessel to the outside thereof.

[Function and Effect]

As the method uses a liquid vessel capable of holding the liquid therein and a feeding mechanism capable of feeding the liquid of said liquid vessel to said sample vessel, so that an amount of the liquid exceeding said approximately fixed amount is caused to overflow from said sample vessel to the outside thereof, even if the amount of liquid fed by the feeding mechanism to the sample vessel exceeds the approximately fixed amount, the sample vessel can hold therein the approximately fixed amount of liquid remaining therein.

Therefore, without effecting a measurement in advance, an approximately fixed amount of liquid can be charged into the sample vessel, so that precision detection is readily possible, when needed, under the predetermined condition, without requiring any special skill or experience.

BEST MODE OF EMBODYING THE INVENTION

Next, an embodiment of the present invention will be described with reference to the accompanying drawings.

FIGS. 1 through 12 show an inventive detecting apparatus for detecting a volatile dissolved substance. The apparatus includes a sample vessel 1 capable of selectively holding therein an approximately fixed amount of reference liquid A such as distilled water or an approximately fixed amount of detection target liquid B from which the volatile dissolved substance is to be detected, with leaving a free space C at an upper inner section thereof, a reference liquid vessel 2 capable of holding the reference liquid A therein, and a detection target liquid vessel 3 capable of holding the detection target liquid B therein, with these vessels being closable/sealable. In addition to these, the detecting apparatus further includes a feeding mechanism D capable of selectively feeding the reference liquid A of the reference liquid vessel 2 or the detection target liquid B of the detection target liquid vessel 3 and an overflow mechanism E for causing an excess amount of either the reference liquid A or the detection target liquid B exceeding the approximately fixed amount to overflow from the sample vessel 1 to the outside thereof. Further, the sample vessel 1 includes a nozzle 4 made of e.g. a porous glass ball capable of bubbling for blowing off bubbles into the reference liquid A or the detection target liquid B whichever is held within the sample vessel 1.

Within an upper communicating pipe passage 5 communicated with an upper section of the sample vessel 1, there is exposed a detecting portion of a gas sensor S capable of detecting the volatile component. Further, there are provided a sensor controlling portion 6 for controlling the operation of the gas sensor S and a data processing portion 7 for processing detection data obtained by the gas sensor S and displaying the detection result. In operation, the volatile component evaporated from the reference liquid A or the detection target liquid B in the sample vessel 1 is guided into the upper communicating pipe passage 5 to be detected by the gas sensor S. Then, the detection result obtained by the gas sensor S on a reference volatile component evaporated from the reference liquid A or on a detection target volatile component evaporated from the detection target volatile component evaporated from the detection target liquid B are compared with each other, whereby the volatile dissolved substance dissolved in the detection target liquid B can be detected.

The upper communicating pipe passage 5 incorporates, at a mid of its extension, a first three-way valve V1, so that the passage 5 can be switched over to one of a condition where a first communicating pipe passage 5a wherein the detecting portion is exposed is communicated with a second communicating pipe passage 5b on the side of the sample vessel 1 and a further condition wherein the second communicating pipe passage 5b is closed and the first communicating pipe passage 5a is communicated with the outside of the vessel, and a still further condition wherein the second communicating pipe passage 5b is closed and the communication between the first communicating pipe passage 5a and the outside of the vessel is also shut off.

The overflow mechanism E includes an overflow pipe 8 communicated and connected with the sample vessel 1 and constructed such that an excess amount of the reference liquid A or the detection target liquid B exceeding the approximately fixed amount is caused to overflow from the sample vessel 1 through this overflow pipe 8 to the outside of the vessel. Also, in this overflow mechanism E, the overflow pipe 8 and a first drain discharging pipe passage F1 communicated with the outside of the vessel is interconnected via a second three-way valve V2, so that the mechanism can be switched over between a condition wherein the first drain discharging pipe passage F1 is communicated and connected with the overflow pipe 8 and a further condition wherein the overflow pipe 8 is closed and the first drain discharging pipe passage F1 is communicated and connected with the outside of the vessel.

The feeding mechanism D includes a liquid valve mechanism H capable of selectively communicating/connecting one of a reference liquid feeding pipe passage G1 extending from the reference liquid vessel 2 to the sample vessel 1, a detection target liquid feeding pipe passage G2 extending from the detection target liquid vessel 3 to the sample vessel 1 and a second drain discharging pipe passage (liquid discharging passage) F2 communicated with the outside of the vessel, to a lower end of the sample vessel 1. And, a starting end of the reference liquid feeding pipe passage G1 is inserted to a position near the bottom face of the reference liquid vessel 2 whereas a starting end of the detection target liquid feeding pipe passage G2 is inserted to a position near the bottom face of the detection target liquid vessel 3. Hence, in response to a valve switchover operation of the liquid valve mechanism H, the reference liquid A in the reference liquid vessel A pressurized with pressured air (an example of "pressurized gas") or the detection target liquid B in the detection target liquid vessel B pressurized with the pressurized air can be selectively force-fed into the sample vessel 1 through a lower communicating pipe passage 9. Further, the feeding mechanism D is capable of discharging the liquid in the sample vessel 1 to the outside of this vessel through the second drain discharging pipe passage F2.

The liquid valve mechanism H includes a third three-way valve V3 for selectively connecting the reference liquid feeding pipe passage G1 or the detection target liquid feeding pipe passage G2 to a first intermediate feeding pipe passage J1, a fourth three-way valve V4 for selectively connecting the first intermediate feeding pipe passage J1 or the second drain discharging pipe passage F2 to a second intermediate feeding pipe passage J2 and a fifth three-way valve V5 for selectively connecting the lower communicating pipe passage 9 of the sample vessel 1 or a third drain discharging pipe passage F3 communicated with the outside of the vessel, to the second intermediate feeding pipe passage J2.

Further, there is provided a pressurized air feeding device L having a pressurized air feeding mechanism K for compressing clean air past a filter or the like by e.g. a compressor and reserving this compressed air in an air tank 10 and then feeding this compressed or pressurized air in the air tank 10 to the nozzle 4 or the various liquid vessels 2, 3, so that the pressurized air (an example of "pressurized gas") for blowing off can be fed to the nozzle 4 or the pressurized air can be fed to the reference liquid vessel 2 or the detection target liquid vessel 3.

In the pressurized air feeding mechanism K, an air feeding pipe M connected to the air tank 10 is branched into a first air feeding pipe M1 for feeding the pressurized air to the nozzle 4 and a second air feeding pipe M1 for feeding the pressurized air to the reference liquid vessel 2 and the detection target liquid vessel 3. To each one of the first and second air feeding pipes M1, M2, there are connected a needle valve 11 and a flow meter 12 in this order from the upstream side. With this, the pressurized air feeding mechanism K can be switched over between a condition wherein the first air feeding pipe M1 is communicated and connected with a nozzle side air pipe 13 by connecting this nozzle side air pipe 13 connected with the nozzle 4 to the first air feeding pipe M1 via a sixth three-way valve V6 and a further condition wherein the nozzle side air pipe 13 is closed so as to shut off the inflow of pressurized air from the first air feeding pipe M1 and the communication between the first air feeding pipe M1 and the outside of the vessel is also shut off. Further, a vessel side air pipe 14 branched and connected to an upper inner space of the reference liquid vessel 2 and an upper inner space of the detection target liquid vessel 3 are connected with each other via a seventh three-way valve V7, so that the mechanism can be switched over between a condition wherein the vessel side air pipe 14 is communicated and connected with the second air feeding pipe M2 and a further condition wherein the second air feeding pipe M2 is closed and the vessel side air pipe 14 is communicated and connected with the outside of the vessel.

Incidentally, to each one of the first and second air feeding pipes M1, M2, the needle valve 11 and the flow meter 12 can be connected in this order from the downstream side.

The gas sensor S comprises a metal oxide semiconductor type gas sensor, whose detecting portion (sensing element) comprises a so-called sintered type gas-sensitive body made mainly of a metal oxide semiconductor such as tin oxide ($SnO_2$) and formed into a substantially spherical shape. And, inside this gas-sensitive body, there is embedded a heater/electrode made of platinum coil-like element, and inside the gas-sensitive body and extending through the center of the heater-electrode, there is also embedded a resistance detecting electrode made of a precious metal wire. The sensor controlling portion 6 controls heating of the heater/electrode of the sensing element. The data processing portion 7 is configured to detect the volatile component, based on resistance variation in the gas-sensitive body.

The gas-sensitive body was formed by causing tin oxide as the major component to carry therein 1.5 wt % of palladium (Pd). Referring more particularly to this gas-sensitive body, aqueous solution of tin chloride ($SnCl_4$) was hydrolyzed with ammonia ($NH_3$) to obtain tin oxide sol. The resultant tin oxide sol was air-dried and then sintered in the air for one hour at e.g. 500° C., soaked in aqua regia solution of palladium and sintered in the air for one hour at e.g. 500° C., thus causing the tin oxide to carry the palladium. Then, this palladium-carrying tin oxide was mixed with an equal amount of 1000-mesh alumina as aggregate. Further, to the resultant mixture, terpineol was added to render the mixture into paste. Thereafter, this paste obtained was applied to the heater/electrode and the resistance detecting electrode and sintered for one hour in the air at 500° C. for instance, whereby the gas-sensitive body was completed.

Incidentally, the above-described components, such as the sample vessel 1 and the reference liquid vessel 2, the detection target liquid vessel 3, the overflow pipe 8, the various pipe passages 5, 9, F1 through F3, G1, G2, J1, J2, the various air pipes 13, 14, the air feeding pipes M1, M1, M2, etc. are formed of materials such as glass, Teflon (registered trademark) resin, which do not adsorb the volatile components to be detected.

Next, a method of operating the above-described detecting apparatus will be described.

The reference liquid vessel will hold therein the reference liquid A such as pure water, and the detection target liquid vessel 3 will hold therein the detection target liquid B. Then, the first through seventh three-way valves V1 through V7 will be switched over, as illustrated in FIG. 1. More particularly, the second three-way valve V2 will communicate the overflow pipe 8 with the first drain discharging pipe passage F1.

Also, the third through fifth three-way valves V3 through V5 will communicate the reference liquid vessel 2 and the empty sample vessel 1 with each other via the reference liquid feeding pipe passage G1, the first intermediate feeding pipe passage J1 and the second intermediate feeding pipe passage J2 and the lower communicating pipe passage 9. The first three-way valve V1 will shut off the communication between the first communicating pipe passage 5a and the second communicating pipe passage 5b. The sixth three-way valve V6 will shut off the communication between the first air feeding pipe passage M1 and the nozzle side air pipe 13. The seventh three-way valve V7 will shut off the communication between the second air feeding pipe M2 and the vessel side air pipe 14.

Next, as illustrated in FIG. 2, the seventh three-way valve V7 will be switched over to communicate the vessel side air pipe 14 to the second air feeding pipe M2, thus feeding the pressurized air to the reference liquid vessel 2. Any excess reference liquid A will be caused to overflow from the overflow pipe 8, so that the sample vessel 1 will hold therein an approximately fixed amount of reference liquid A remaining therein, with leaving the free space C at the inner upper section.

Next, as illustrated in FIG. 3, the fourth and fifth three-way valves V4 and V5 will be switched over so as to communicate the second intermediate feeding pipe passage J2 with the second drain discharging pipe passage F2 and the third drain discharging pipe passage F3, thus shutting off the communication between the reference liquid vessel 2 and the sample vessel 1. Along with this, the seventh three-way valve V7 will be switched over to establish communication between the vessel side air pipe 14 and the outside of the vessel, thus stopping supply of the pressurized air to the reference liquid vessel 2. Further, in order to render approximately constant the amount of reference liquid A in the sample vessel 1 during bubbling, the sixth three-way valve V6 will be switched over to communicate the nozzle side air pipe 13 with the first air feeding pipe M1, thus generating bubbles so as to cause the reference liquid A in the sample vessel 1 to overflow from the overflow pipe 8.

Next, as illustrated in FIG. 4, the second three-way valve V2 will be switched over so as to close the overflow pipe 8 by shutting off the communication between the overflow pipe 8 and the first drain discharging pipe passage F1. Further, the first three-way valve V1 will be switched over to establish communication between the first communicating pipe passage 5a and the second communicating pipe passage 5b, thereby guiding the reference volatile component which has been evaporated from the reference liquid A by the bubbling from the nozzle 4, into the upper communicating pipe passage 5. Then, the gas sensor S will detect this reference volatile component and the data processing portion 7 will process the resultant detection data and store the detection result in a memory or the like and also display on e.g. a liquid crystal monitor.

Next, as illustrated in FIG. 5, the first three-way valve V1 will be switched over to shut off the communication between the first communicating pipe passage 5a and the second communicating pipe passage 5b, thereby shutting of the second communicating pipe passage 5b. Further, the fifth three-way valve V5 will be switched over so as to communicate the lower communicating pipe passage 9 with the second intermediate feeding pipe passage J2, thus discharging the reference liquid A in the sample vessel 1 to the outside of the vessel through the second drain discharging pipe passage F2.

Next, as illustrated in FIG. 6, the second three-way valve V2 will be switched over so as to establish communication between the overflow pipe 8 and the first drain discharging pipe passage F1. Also, the third and fourth three-way valves V3, V4 will be switched over so as to establish communication between the detection target liquid vessel 3 and the empty sample vessel 1 through the detection target liquid feeding pipe passage G2, the first intermediate feeding pipe passage J1, the second intermediate feeding pipe passage J2 and the lower communicating pipe passage 9. Further, the sixth three-way valve V6 will be switched over for shutting off the communication between the nozzle side air pipe 13 and the first air feeding pipe M1. And, the seventh three-way valve V7 will be switched over so as to communicate the vessel side air pipe 14 with the second air feeding pipe M2, thereby feeding the pressurized air to the detection target liquid vessel 3 and feeding the detection target liquid B to the sample vessel 1. Any excess detection target liquid B will be caused to overflow from the overflow pipe 8, whereby an approximately fixed amount of detection target liquid B will be held within the sample vessel 1.

Next, as illustrated in FIG. 7, the fourth and fifth three-way valves V4, V5 will be switched over so as to communicate the second intermediate feeding pipe passage J2 with the second drain discharging pipe passage F2 and the third drain discharging pipe passage F3, thereby shutting off the communication between the detection target liquid vessel 3 and the sample vessel 1. Along with this, the seventh three-way valve V7 will be switched over so as to establish communication between the vessel side air pipe 14 and the outside of the vessel, thus stopping the feeding of pressurized air to the sample vessel 9. Further, in order to render approximately fixed the amount of the detection target liquid B held in the detecting liquid 1 at the time of bubbling, the sixth three-way valve V6 will be switched over so as to establish communication between the bubble side air pipe 13 and the first air feeding pipe M1, thus generating bubbles for causing the detection target liquid B in the sample vessel 1 to overflow from the overflow pipe 8.

Next, as illustrated in FIG. 8, the third and fourth three-way valves V3, V4 will be switched over so as to establish communication between the reference liquid vessel 2 and the third drain discharging pipe passage F3. Also, the seventh three-way valve V7 will be switched over so as to establish communication between the vessel side air pipe 14 and the second air feeding pipe M2. Under this condition, the reference liquid A will be introduced to the first intermediate feeding pipe passage J1 and the second intermediate feeding pipe passage J2 to be discharged from the third drain discharging pipe passage F3, whereby the first intermediate feeding pipe passage J1 and the second intermediate pipe passage J2 will be cleaned and the remaining-detection target liquid B will be discharged.

Next, as illustrated in FIG. 9, the fourth three-way valve V4 will be switched over so as to communicate the second intermediate feeding pipe passage J2 to the second drain discharging pipe passage F2 and the third drain discharging pipe passage F3, thus shutting off the communication between the reference liquid container 2 and the third drain discharging pipe passage F3. Along with this, the seventh three-way valve V7 will be switched over to communicate the vessel side air pipe 14 with the outside of the vessel, thus stopping the feeding of the pressurized air to the reference liquid vessel 2. And, the second three-way valve V2 will be switched over so as to close the overflow valve 8 by shutting off the communication between the overflow pipe 8 and the first drain discharging pipe passage F1. Further, the first three-way valve V1 will be switched over to establish communication between the first communicating pipe passage 5a and the second communicating pipe passage 5b, thus guiding the detection target volatile component which has been evaporated from the detection target liquid B due to the bubbling from the nozzle 4, into the upper communicating passage 5. And, the data processing portion 7 will process the detection data of the detection target volatile component obtained by the gas sensor S and store the detection result in a memory or the like and also display on e.g. a liquid crystal monitor.

Next, as illustrated in FIG. 10, the first three-way valve V1 will be switched over so as to shut off the communication between the first communicating pipe passage 5a and the second communicating pipe passage 5b, thus shutting off the second communicating pipe passage 5b. Also, the fifth three-way valve V5 will be switched over to establish communication between the lower communicating pipe passage 9 and the second intermediate feeding pipe passage J2, thus causing the detection target liquid B in the sample vessel 1 to be discharged to the outside of the vessel through the second drain discharging pipe passage F2.

Next, as illustrated in FIG. 11, the second three-way valve V2 will be switched over to establish communication between the overflow pipe 8 and the first drain discharging pipe passage F1. Further, the fourth three-way valve V4 will be switched over to establish communication between the reference liquid vessel 2 and the empty sample vessel 1 through the reference liquid feeding pipe passage G1, the first intermediate feeding pipe passage J1, the second intermediate feeding pipe passage J2 and the lower communicating pipe passage 9, thereby feeding the pressurized air to the reference liquid vessel 2 and feeding the reference liquid A to the sample vessel 1. Thereafter, as illustrated in FIG. 12, the second three-way valve V2 will be switched over to shut off the communication between the overflow pipe 8 and the first drain discharging pipe passage F1. Along with this, the fourth three-way valve V4 will be switched over to communicate the lower communicating pipe passage 9 to the second drain discharging pipe passage F2, thus discharging the reference liquid A in the sample vessel 1 to the outside of the vessel through the second drain discharging pipe passage F2. By repeating these operations for a plurality of times (2 to 3 times), the inside of the sample vessel 1 will be cleaned.

Next, according to the procedure illustrated in FIGS. 1 through 4, for the reference liquid A, its reference volatile component will again be detected by the gas sensor S. And, the data processing portion 7 will process the detection data and store the detection result in a memory or the like and also display on e.g. a liquid crystal monitor.

And, in the data processing portion 7, the detection data of the detection target volatile component and the detection data of the reference volatile component obtained before or after the detection of the detection target volatile component will be compared to each other, thus determining presence/absence of volatile dissolved substance dissolved in the detection target liquid B and its dissolution amount and displaying the presence/absence and the dissolution amount on the liquid crystal monitor or the like.

Other Embodiments

1. The inventive detecting apparatus for volatile dissolved substance can be used not only for detection of a volatile organic compound a trace amount of which can be a cause for stench or unwanted flavor in raw water such as mineral water, soft drink, etc, but also for detection of a volatile organic compound present in waste water from a sewage plant, various industrial plants, etc.

2. The inventive detecting apparatus for volatile dissolved substance can employ, as the sensor, a hot-wire gas sensor, a solid electrolyte type gas sensor, an infrared type gas sensor, etc.

3. The inventive detecting apparatus for volatile dissolved substance can include an overflow mechanism configured to feed the excess liquid exceeding the approximately fixed amount from an upper opening of the sample vessel, thus causing it to overflow to the outside of the vessel.

4. The inventive detecting apparatus for volatile dissolved substance can include combination of a liquid vessel for holding reference liquid and a sample vessel for holding only the reference liquid of this liquid vessel and a further combination of a liquid vessel for holding detection target liquid and a sample vessel for holding only the detection target liquid of this liquid vessel.

5. The inventive detecting apparatus for volatile dissolved substance can include a single liquid container and a feeding mechanism capable of feeding only the liquid of this single liquid vessel to the sample vessel.

In this case, for the comparison between the detection result of the reference volatile component and the detection result of the detection target volatile component, the liquid vessel can be configured to be capable of selectively holding therein either the reference liquid or the detection target liquid. Or, two detecting apparatuses, one in which the liquid vessel thereof holds the reference liquid and the other in which the liquid vessel thereof holds the detection target liquid, may be employed for enabling the detection of the volatile dissolved substance in the detection target liquid.

6. The inventive detecting apparatus for volatile dissolved substance can be modified such that the first through seventh three-way valves V1 through V7 described in the disclosed embodiment are manually switchable. Alternatively, the apparatus can include a controlling device for controlling the switchover operations of the first through seventh valves V1 through V7 in such a manner as to allow the operably linked operations of the feeding mechanism D, the overflow mechanism E and the pressurized air feeding mechanism K disclosed in the embodiment.

7. In the inventive detecting apparatus for volatile dissolved substance, the reference liquid vessel can employ, as the reference liquid, pure water of detection target liquid which has been subjected to an adsorbing treatment of odorous component by means of an adsorbent such as activated carbon.

Incidentally, when the detection target liquid subjected in advance to the adsorbing treatment is employed as the reference liquid, the detection target liquid may be held in the reference liquid vessel together with an adsorbent. Or, detection target liquid which has been subjected to an adsorbing treatment by means of e.g. activated carbon may be held in the reference liquid vessel.

INDUSTRIAL APPLICABILITY

The detecting apparatus for volatile dissolved substance according to the present invention is capable of detecting volatile component easily and with high precision under a predetermined condition. Therefore, this apparatus can be used not only for detection of a volatile organic compound a trace amount of which can be a cause for an stench or unwanted flavor in raw water such as mineral water, soft drink, etc, but also for detection of a volatile organic compound present in waste water from a sewage plant, various industrial plants, etc.

BRIEF DESCRIPTION OF THE DRAWINGS

FIG. 1 a schematic view of a detecting apparatus for volatile dissolved substance,
FIG. 2 a schematic view of the detecting apparatus for volatile dissolved substance,
FIG. 3 a schematic view of the detecting apparatus for volatile dissolved substance,
FIG. 4 a schematic view of the detecting apparatus for volatile dissolved substance,
FIG. 5 a schematic view of the detecting apparatus for volatile dissolved substance,
FIG. 6 a schematic view of the detecting apparatus for volatile dissolved substance,
FIG. 7 a schematic view of the detecting apparatus for volatile dissolved substance,
FIG. 8 a schematic view of the detecting apparatus for volatile dissolved substance,
FIG. 9 a schematic view of the detecting apparatus for volatile dissolved substance,
FIG. 10 a schematic view of the detecting apparatus for volatile dissolved substance,
FIG. 11 a schematic view of the detecting apparatus for volatile dissolved substance,
FIG. 12 a schematic view of the detecting apparatus for volatile dissolved substance.

Figure 2:
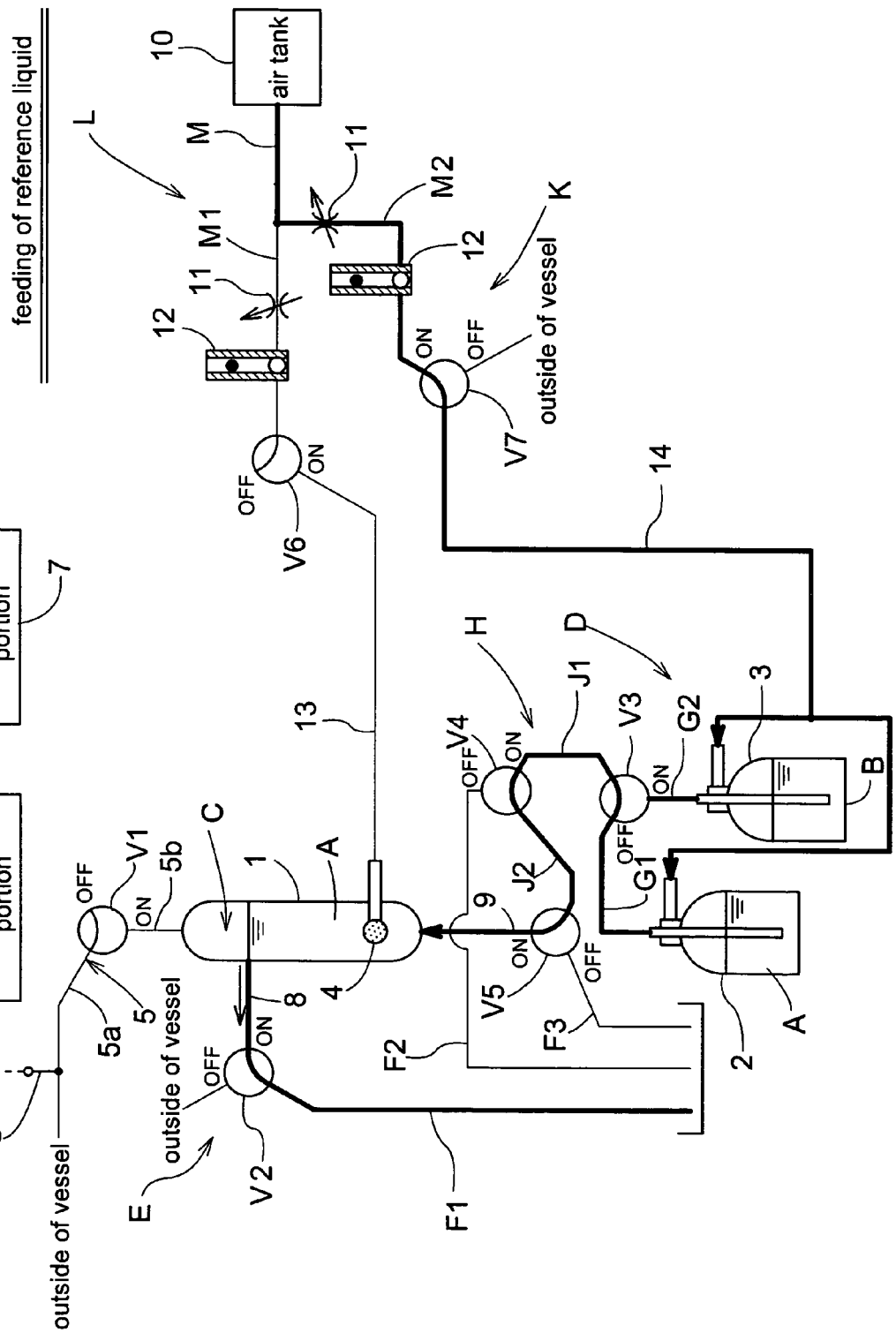
Figure 3:
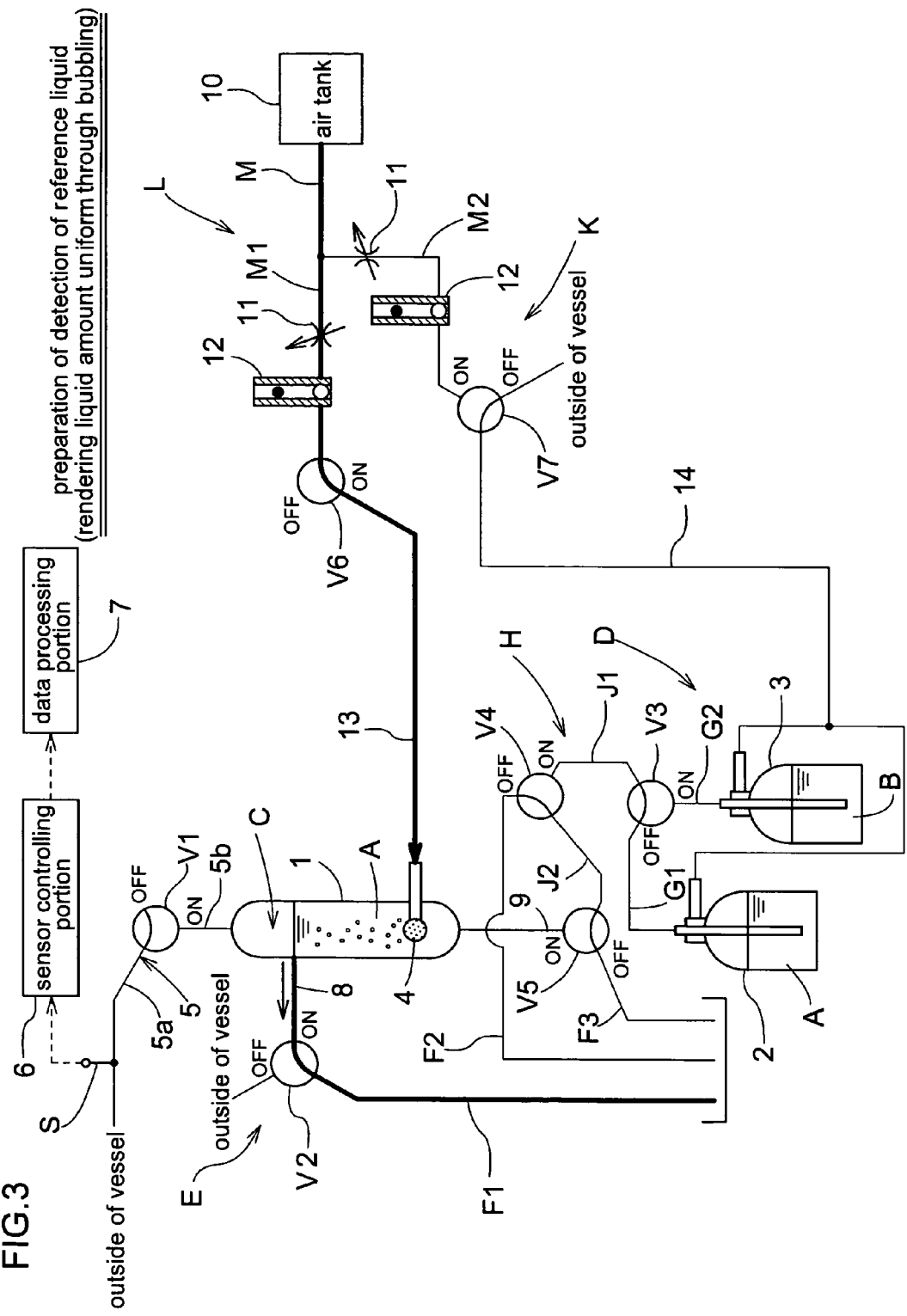
Figure 4:
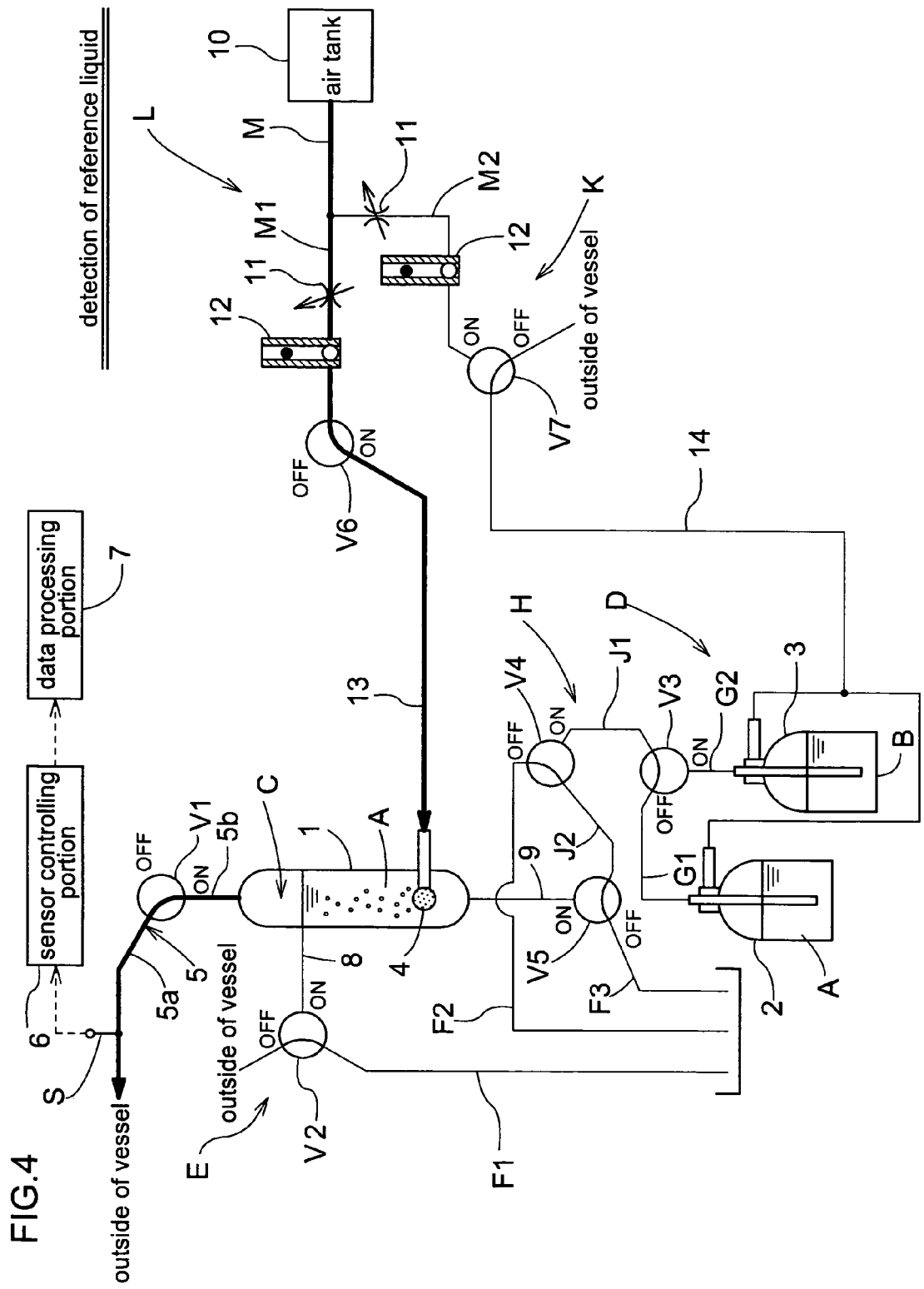
Figure 5:
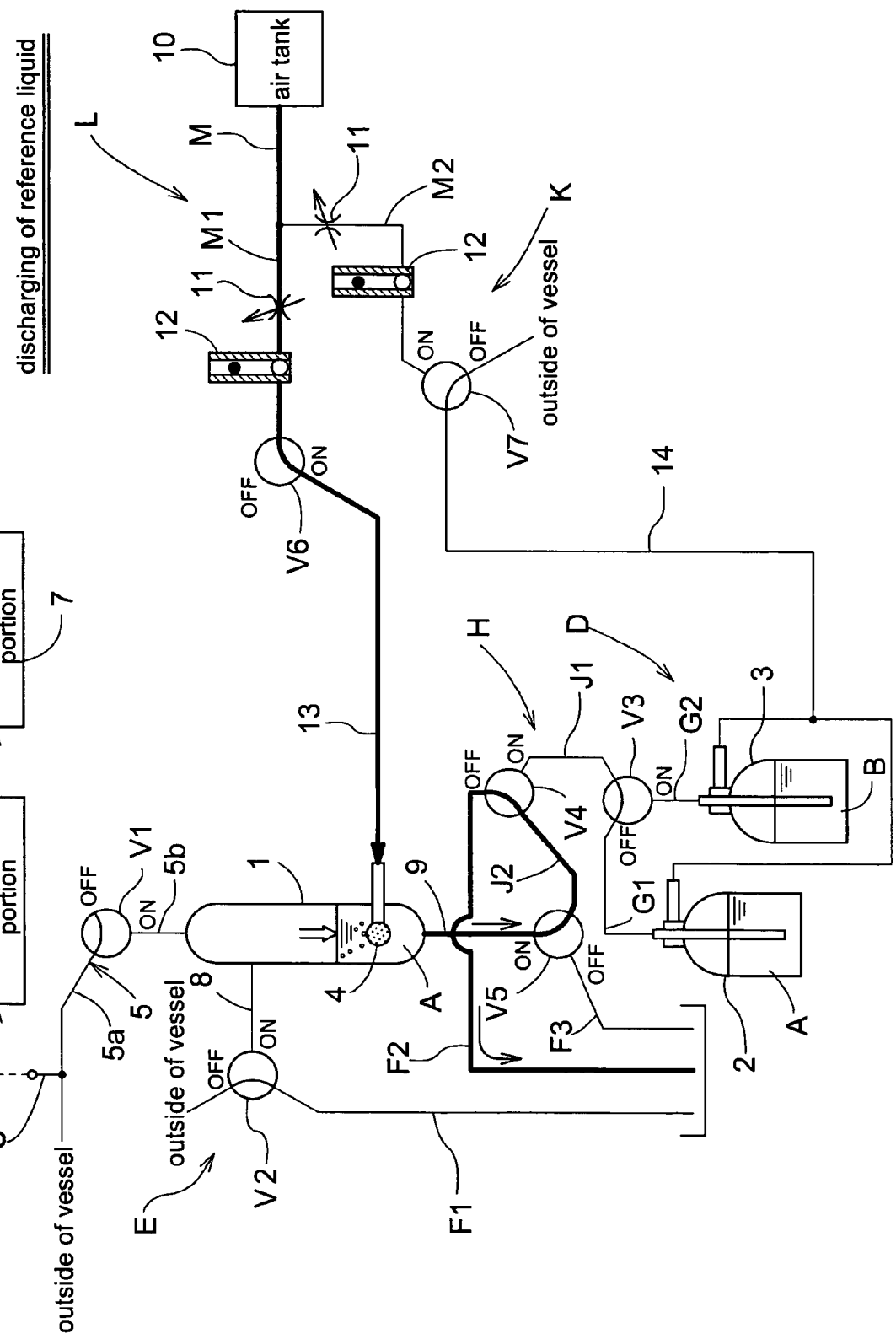
Figure 6:
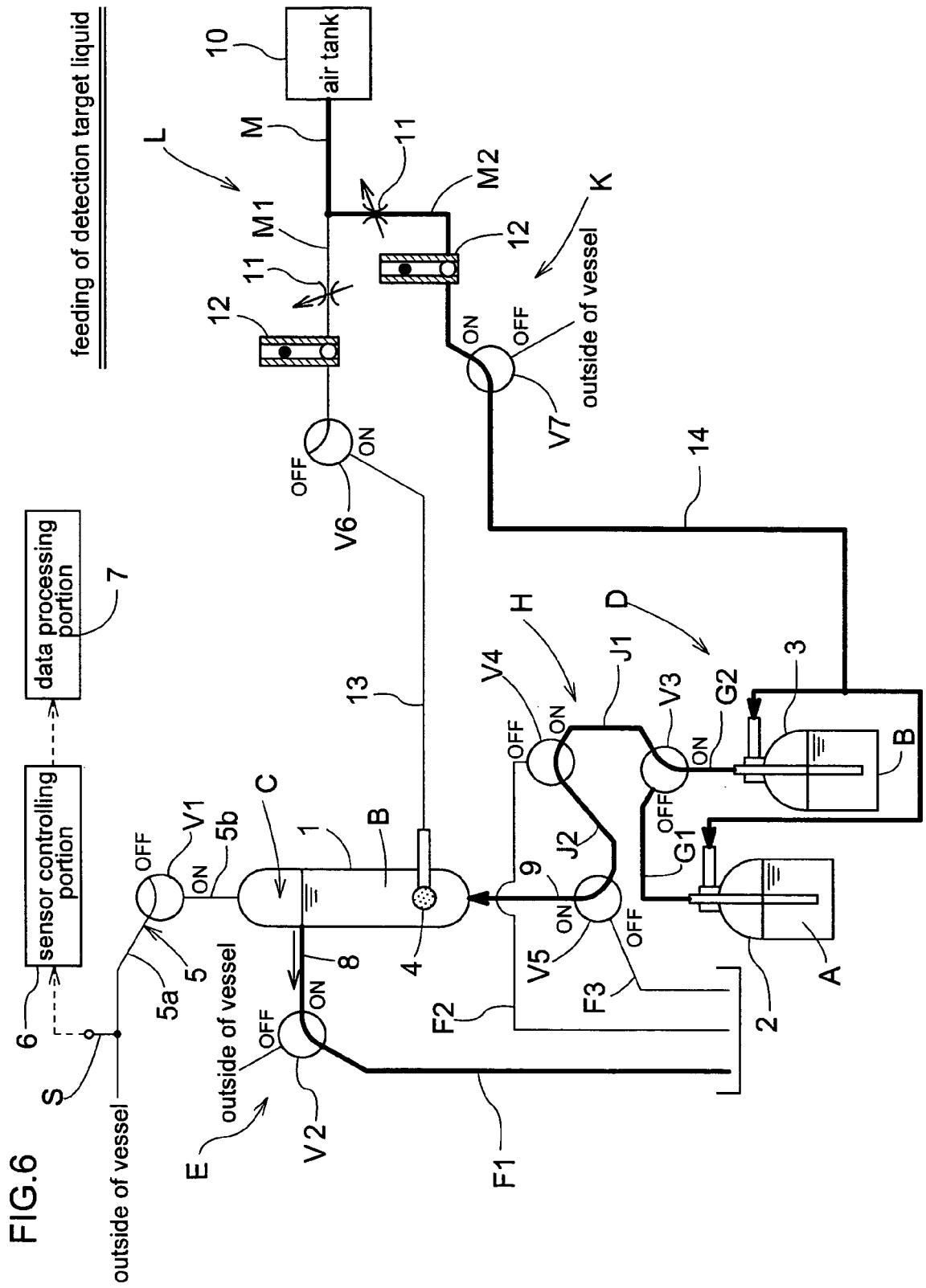
Figure 7:
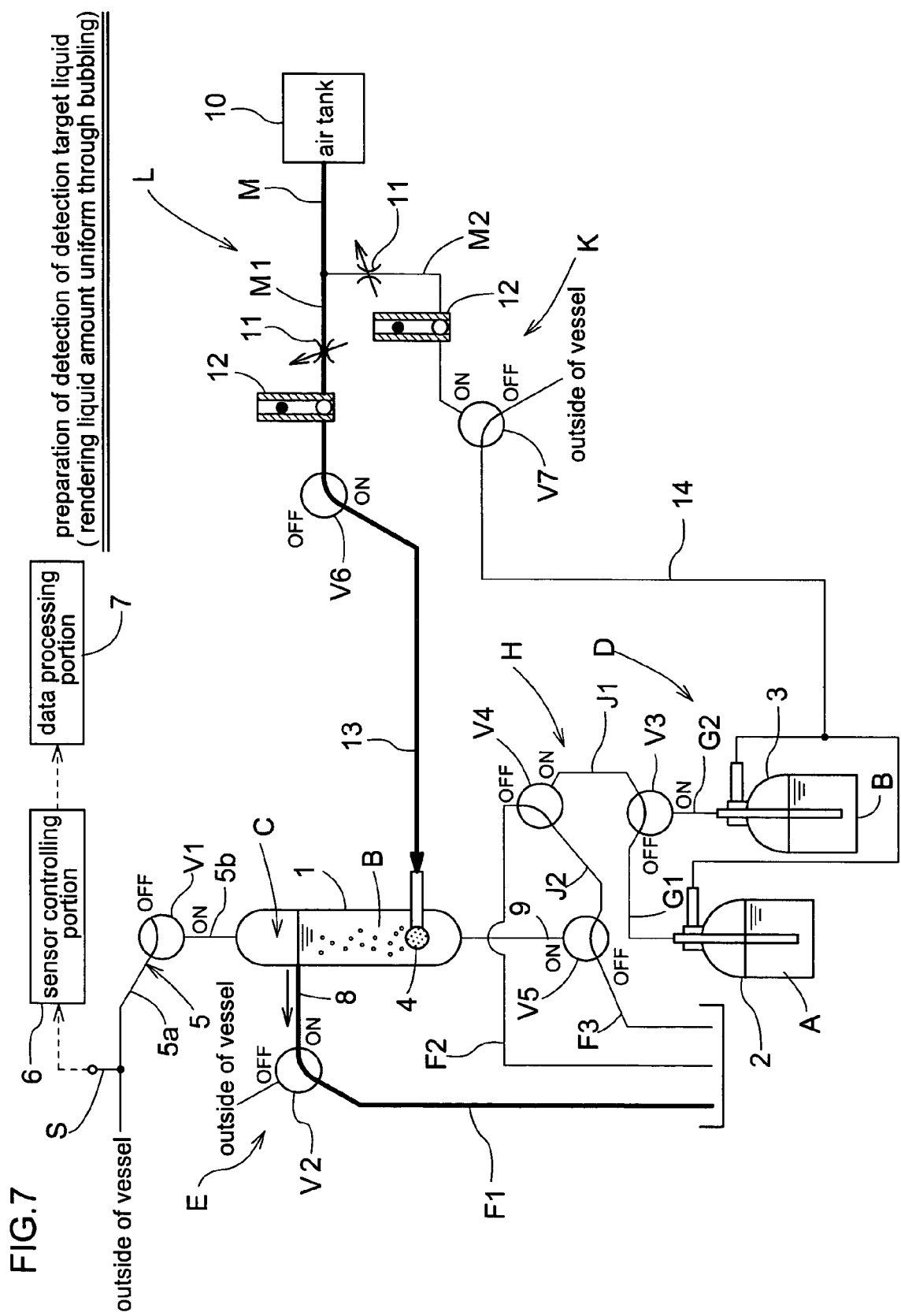
Figure 8:
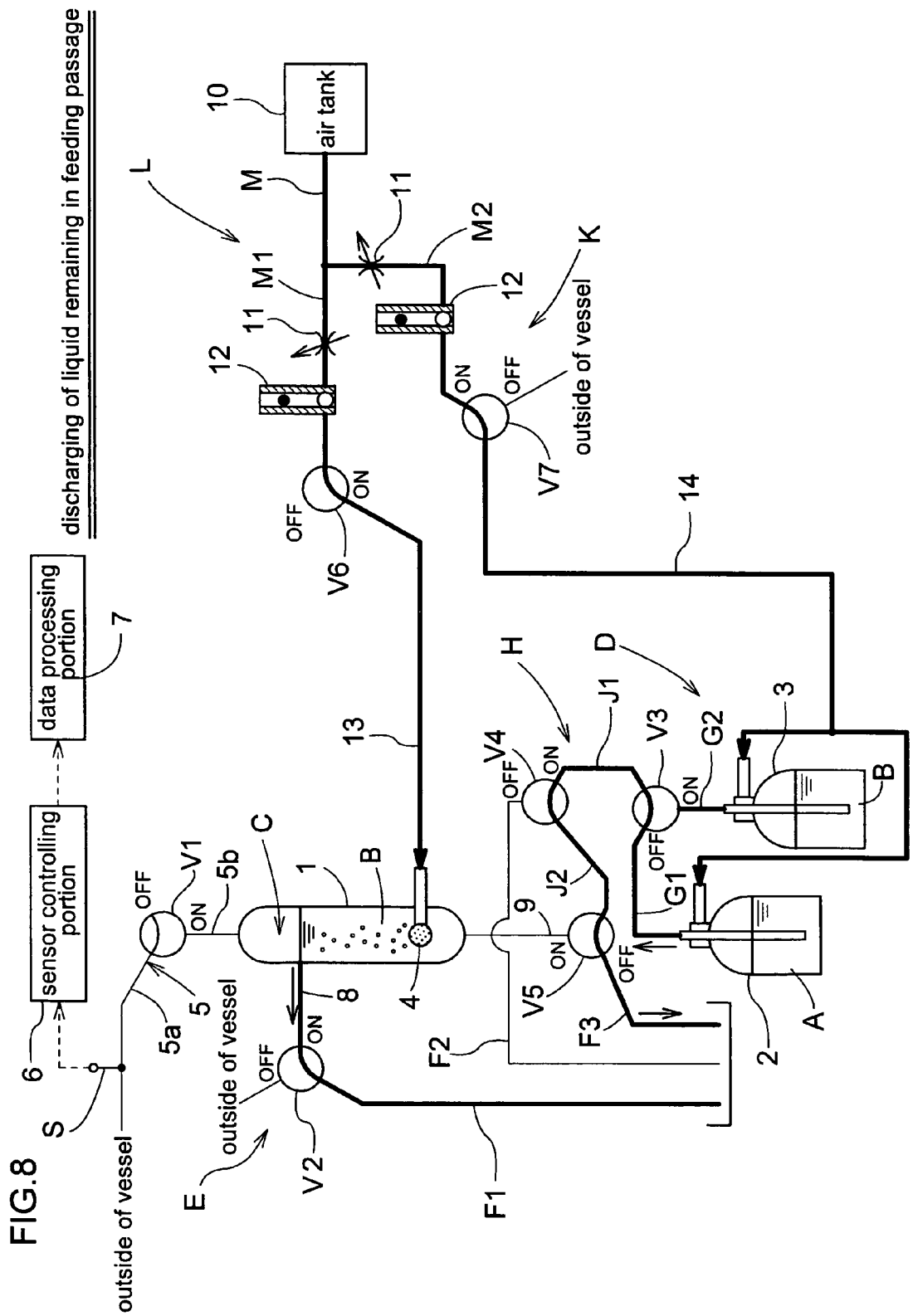
Figure 9:
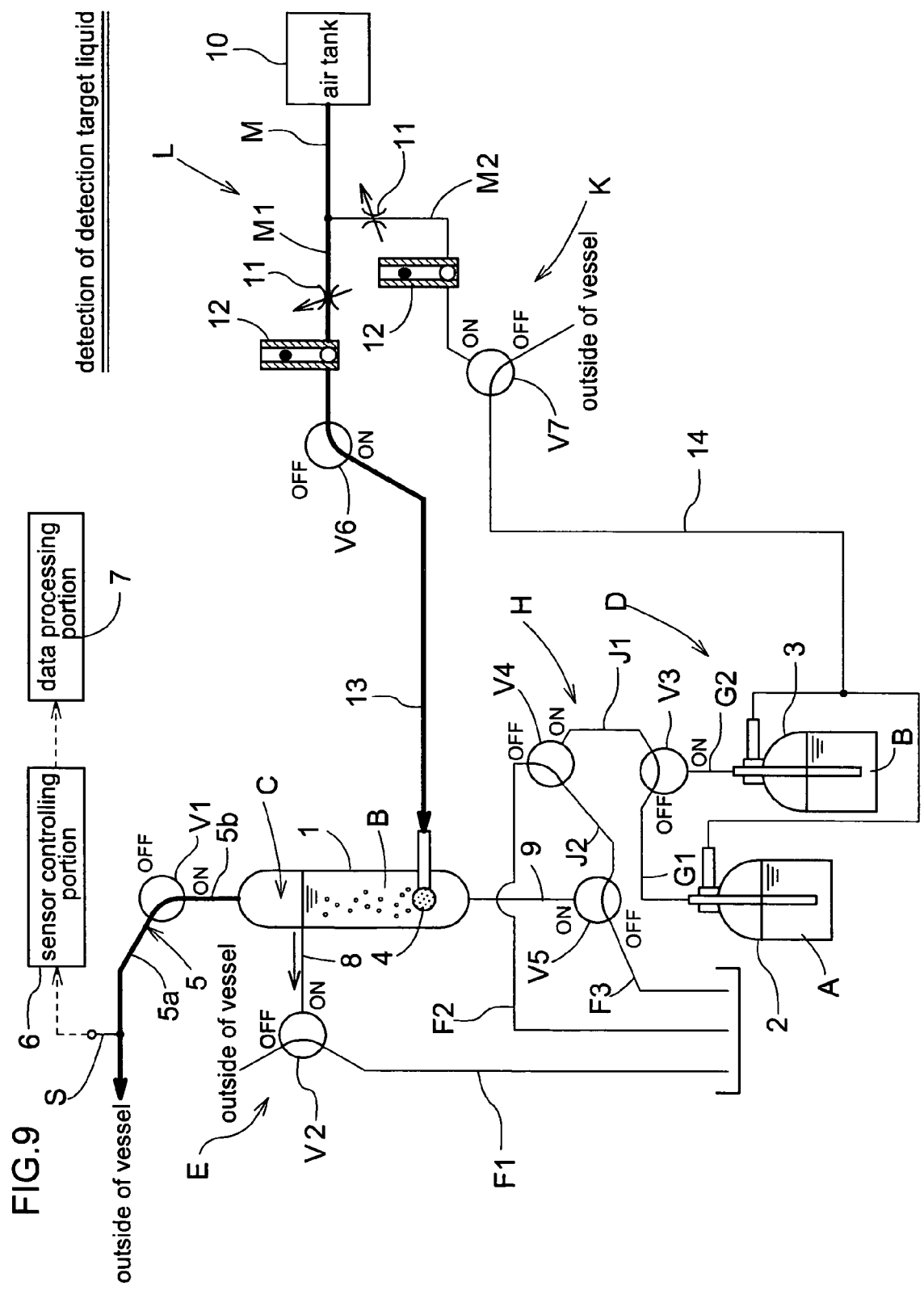
Figure 10:
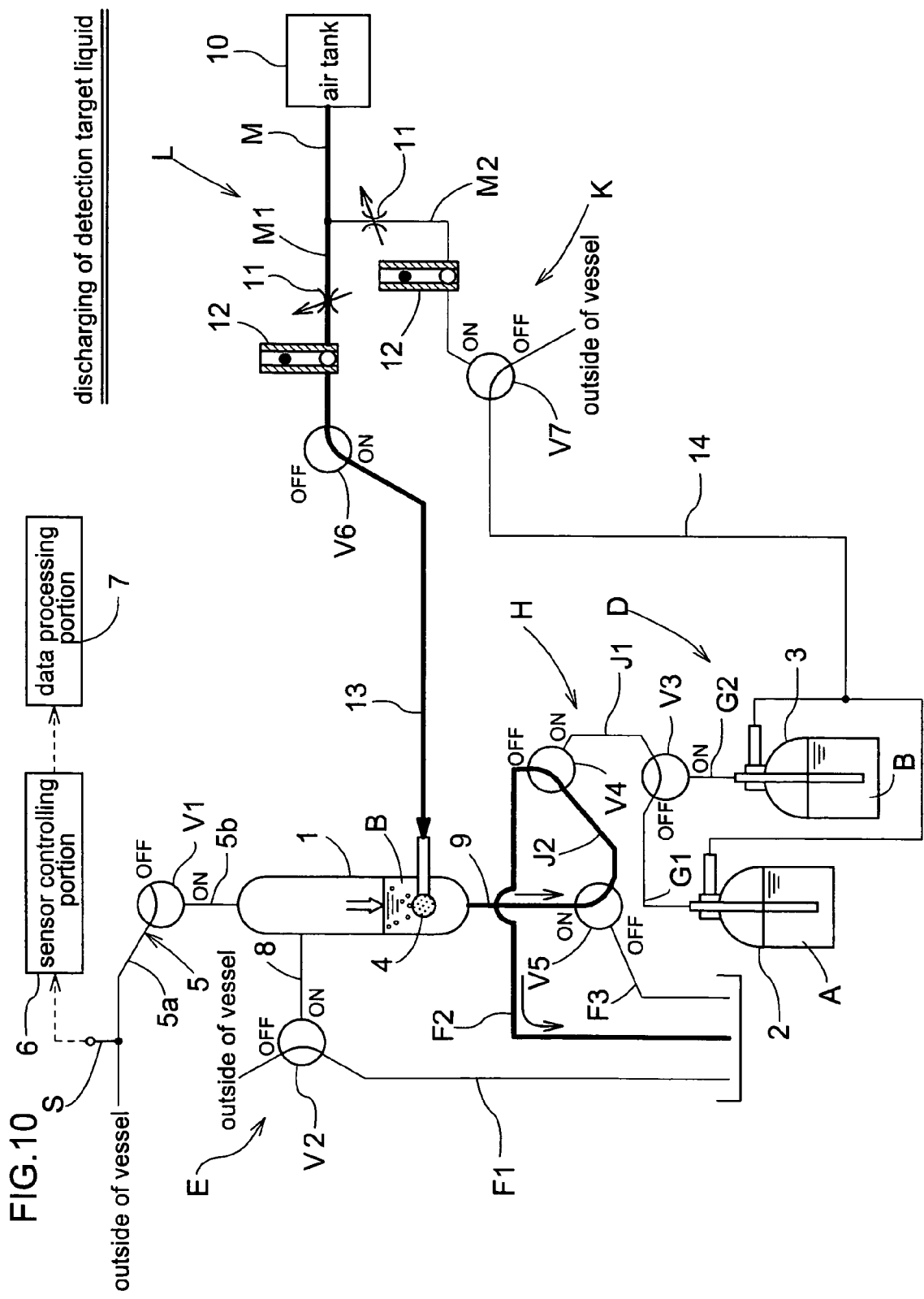
Figure 11:
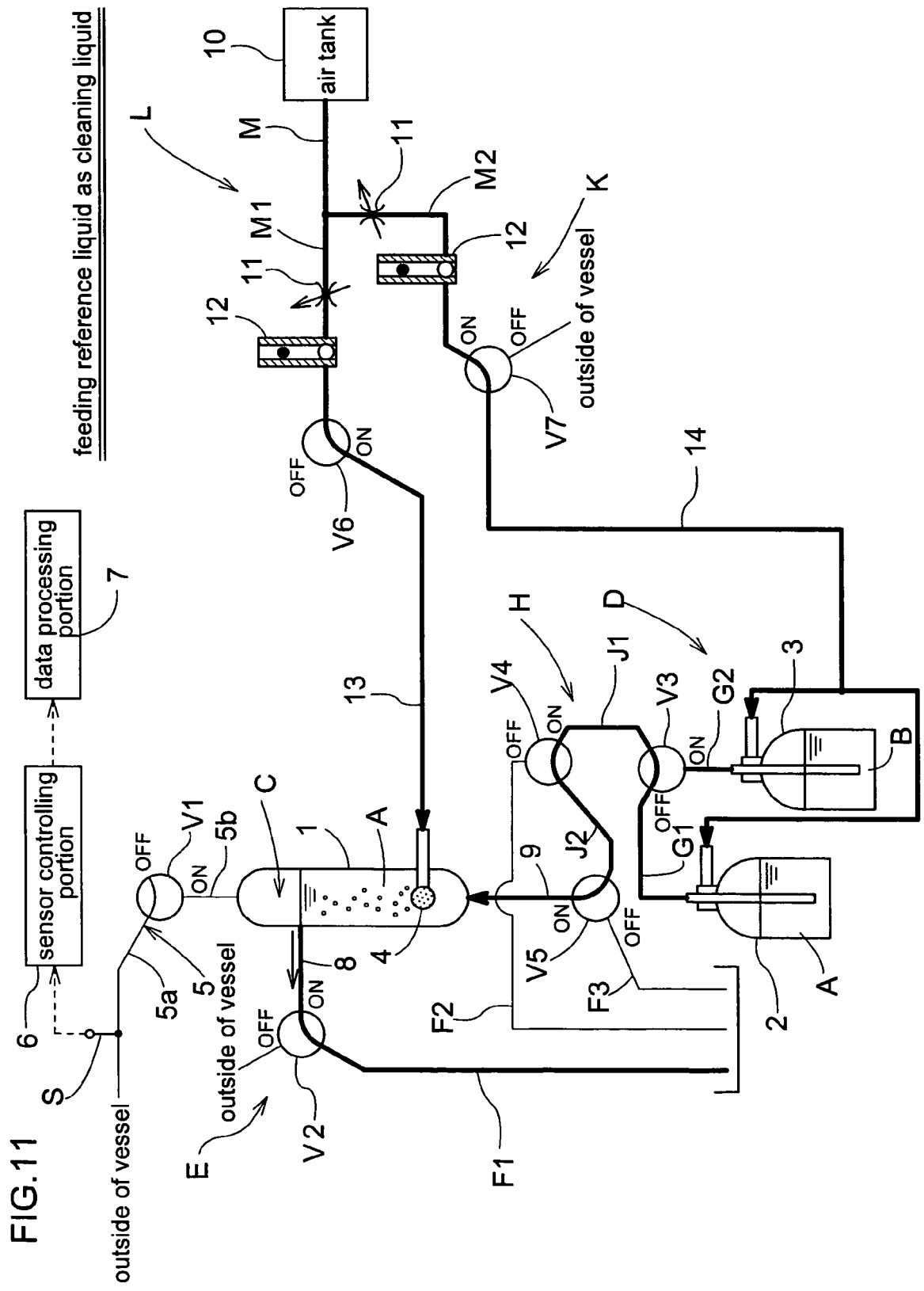
Figure 12:
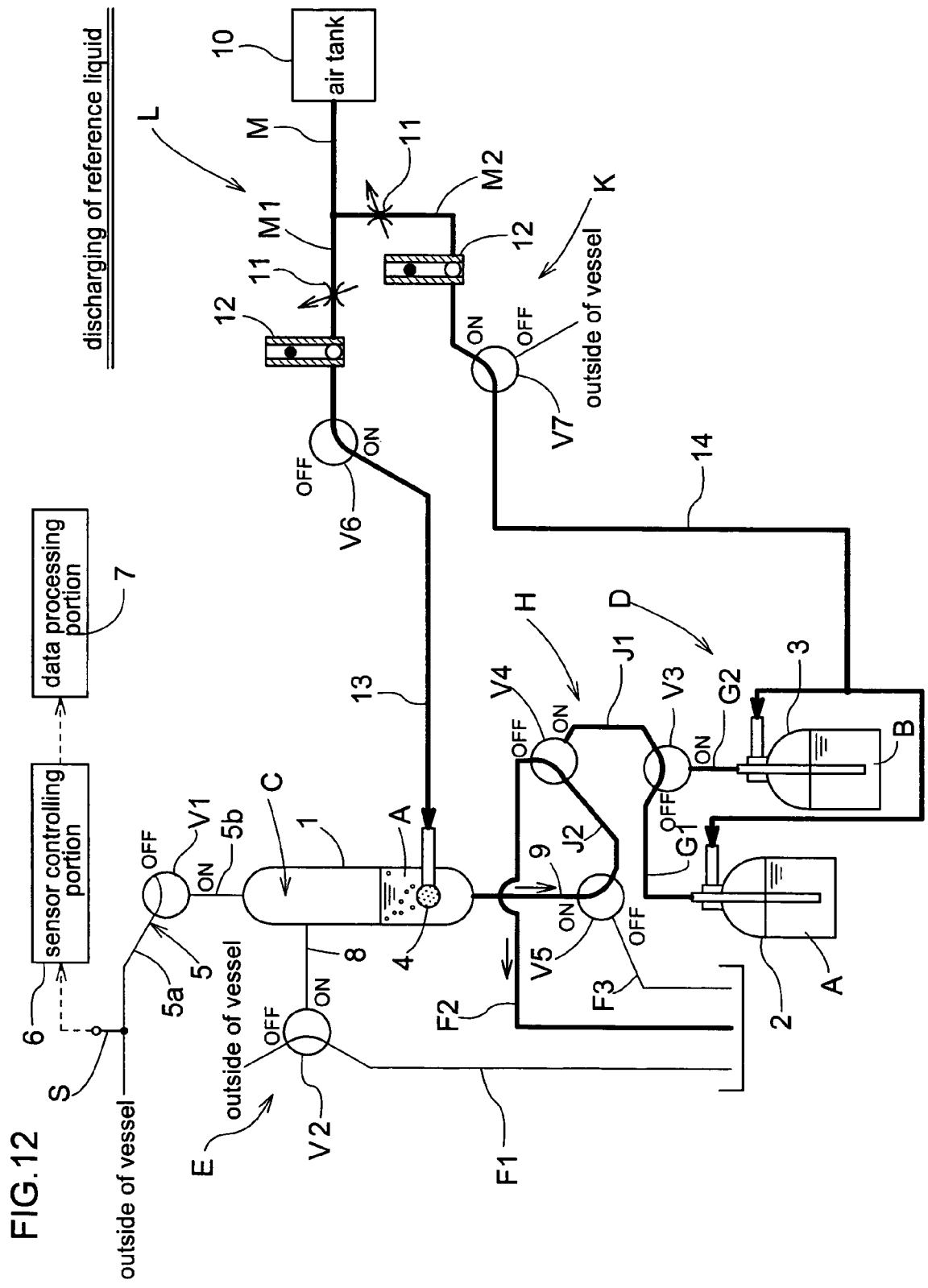

DESCRIPTION OF THE REFERENCE MARKS 1 sample vessel
2 reference liquid vessel
3 detection target liquid vessel
4 nozzle
5 communicating passage
8 overflow pipe
A reference liquid
B detection target liquid
C free space
D feeding mechanism
E overflow mechanism
F2 liquid discharging passage
G1 pipe passage
G2 pipe passage
H valve mechanism
L pressurized gas feeding apparatus
S sensor
V2 valve

The invention claimed is:

1. An apparatus for detecting a volatile dissolved substance, comprising:
   a sample vessel capable of holding therein an approximately fixed amount of liquid with leaving a space at an upper inner section thereof;
   a nozzle capable of blowing off bubbles into the liquid held in the sample vessel;
   a pressurized gas feeding device capable of feeding pressurized gas to said nozzle for the blowing of the bubbles;
   wherein within a communication passage communicating with the upper section of the sample vessel, there being exposed a detecting portion of a sensor capable of detecting a volatile component, so that the sensor can detect the volatile component which has evaporated from the liquid in the sample vessel and entered the communication passage;
   at least one liquid vessel capable of holding the liquid therein;
   a feeding mechanism capable of feeding the liquid of said liquid vessel to said sample vessel;
   an overflow mechanism including an overflow pipe connected with the sample vessel for causing an amount of the liquid exceeding said approximately fixed amount to overflow from said sample vessel to the outside thereof through the overflow pipe;
   a valve capable of selectively connecting a liquid feeding passage from the liquid vessel to the sample vessel and a liquid discharging passage to the sample vessel;
   a valve for opening and closing the communication passage; and
   a valve for opening and closing the overflow pipe;
   wherein when the liquid discharging passage is communicated with the sample vessel, the communication passage and the overflow pipe are shut off, and pressurized gas is fed to the nozzle, the liquid in the sample vessel is discharged to the outside of the sample vessel via the liquid discharging passage.

2. The apparatus for detecting a volatile dissolved substance according to claim 1, said feeding mechanism is constructed such that this feeding mechanism is capable of feeding the liquid to said sample vessel as said pressurized gas feeding device feeds the pressurized gas to the liquid vessel.

3. The apparatus for detecting a volatile dissolved substance according to claim 1, further comprising a data processing section for comparing detection result obtained by said sensor for a reference volatile component evaporated from a reference liquid with detection result obtained by said sensor for a target volatile component evaporated from a detection target liquid, thus detecting the volatile dissolved substance in the liquid and processing detected data.

4. The apparatus for detecting a volatile dissolved substance according to claim 3, wherein said sample vessel is capable of selectively holding therein an approximately fixed amount of the reference liquid or an approximately fixed amount of the detection target liquid.

5. The apparatus for detecting a volatile dissolved substance according to claim 4, wherein the at least one vessel comprises a reference liquid vessel capable of holding the reference liquid therein and a detection target liquid vessel capable of holding the detection target liquid therein, and said feeding mechanism is capable of selectively feeding the reference liquid of the reference liquid vessel or the detection target liquid of the detection target vessel.

6. The apparatus for detecting a volatile dissolved substance according to claim 1, wherein the liquid discharging passage is selectively connectable with the sample vessel via a communicating pipe connected to a lower end portion of the sample vessel.

7. A method for detecting a volatile dissolved substance, comprising the steps of:
   providing at least one liquid vessel and a sample vessel in selective fluid communication with one another via a valve mechanism, the valve mechanism capable of selectively connecting a liquid feeding passage from the liquid vessel to the sample vessel or a liquid discharging passage to the sample vessel;
   feeding liquid in the liquid vessel to the sample vessel by use of a feeding mechanism to reach an approximately fixed amount of the liquid in the sample vessel;
   allowing an amount of the liquid fed to the sample vessel that exceeds the approximately fixed amount to overflow to the outside of the sample vessel through an overflow pipe connected with the sample vessel while leaving a space above the liquid;

feeding pressurized gas by a pressurized gas feeding device to the sample vessel through a nozzle in the sample vessel;

blowing off bubbles into the liquid held in the sample vessel to evaporate a volatile component from the liquid held in the sample vessel;

detecting the volatile component by using a sensor having a detecting portion exposed to the evaporated volatile component via a communication passage;

operating the valve mechanism to allow the liquid discharging passage to be in fluid communication with the sample vessel;

shutting off the communication passage and the overflow pipe; and feeding pressurized gas to the nozzle to discharge the liquid fed to the sample vessel from the sample vessel via the liquid discharging passage.

* * * * *